(12) United States Patent
Tada et al.

(10) Patent No.: US 12,232,763 B2
(45) Date of Patent: Feb. 25, 2025

(54) CATHETER HAVING A SPIRAL DRIVE SHAFT

(71) Applicant: TERUMO KABUSHIKI KAISHA, Tokyo (JP)

(72) Inventors: Yuichi Tada, Santa Clara, CA (US); John Barritt, San Jose, CA (US); Mike Foster, East Palo Alto, CA (US)

(73) Assignee: TERUMO KABUSHIKI KAISHA, Tokyo (JP)

(*) Notice: Subject to any disclaimer, the term of this patent is extended or adjusted under 35 U.S.C. 154(b) by 328 days.

(21) Appl. No.: 17/957,973

(22) Filed: Sep. 30, 2022

(65) Prior Publication Data
US 2024/0090916 A1    Mar. 21, 2024

Related U.S. Application Data

(60) Provisional application No. 63/407,539, filed on Sep. 16, 2022.

(51) Int. Cl.
*A61B 17/3207* (2006.01)
*A61M 25/09* (2006.01)

(52) U.S. Cl.
CPC ..... *A61B 17/320758* (2013.01); *A61M 25/09* (2013.01)

(58) Field of Classification Search
CPC ........... A61B 17/320758; A61B 2017/320052; A61B 2017/320791; A61B 2090/08021; A61B 2217/005; A61B 17/320783; A61B 2017/320766; A61M 25/09
See application file for complete search history.

(56) References Cited

U.S. PATENT DOCUMENTS

| | | | |
|---|---|---|---|
| 4,772,258 A * | 9/1988 | Marangoni | A61B 17/320758 606/159 |
| 7,981,128 B2 | 7/2011 | To et al. | |
| 8,007,506 B2 | 8/2011 | To et al. | |
| 8,070,762 B2 | 12/2011 | Escudero et al. | |
| 8,236,016 B2 | 8/2012 | To et al. | |
| 8,337,516 B2 | 12/2012 | Escudero et al. | |
| 8,361,094 B2 | 1/2013 | To et al. | |
| 8,628,549 B2 | 1/2014 | To et al. | |
| 8,647,355 B2 | 2/2014 | Escudero et al. | |
| 8,795,306 B2 | 8/2014 | Smith et al. | |
| 8,888,801 B2 | 11/2014 | To et al. | |
| 8,920,448 B2 | 12/2014 | To et al. | |
| 9,095,371 B2 | 8/2015 | Escudero et al. | |

(Continued)

*Primary Examiner* — Tan-Uyen T Ho
*Assistant Examiner* — Khoa Tan Le
(74) *Attorney, Agent, or Firm* — Kim & Stewart LLP

(57) ABSTRACT

A catheter for removing an object in a body lumen includes a rotatable drive shaft including a spiral portion having a spiral shape near a distal end of the drive shaft, an outer tube surrounding the drive shaft, a cutting member connected to the distal end of the drive shaft to be rotated by the drive shaft with respect to a rotation axis and by which the object is cut, a guide wire tube attached to a distal portion of the outer tube, extending substantially straight along a center spiral axis of the spiral portion, and having a first guide wire lumen, and a distal tip attached to a distal end of the guide wire tube and having a second guide wire lumen extending parallel to the rotation axis and communicating with the first guide wire lumen.

20 Claims, 8 Drawing Sheets

(56) References Cited

U.S. PATENT DOCUMENTS

| | | |
|---|---|---|
| 9,198,679 B2 | 12/2015 | To et al. |
| 9,308,016 B2 | 4/2016 | Escudero et al. |
| 9,314,263 B2 | 4/2016 | Escudero et al. |
| 9,333,007 B2 | 5/2016 | Escudero et al. |
| 9,345,511 B2 | 5/2016 | Smith et al. |
| 9,492,192 B2 | 11/2016 | To et al. |
| 9,492,193 B2 | 11/2016 | To et al. |
| 9,668,767 B2 | 6/2017 | To et al. |
| 9,675,376 B2 | 6/2017 | To et al. |
| 2015/0141816 A1 | 5/2015 | Gupta et al. |

* cited by examiner

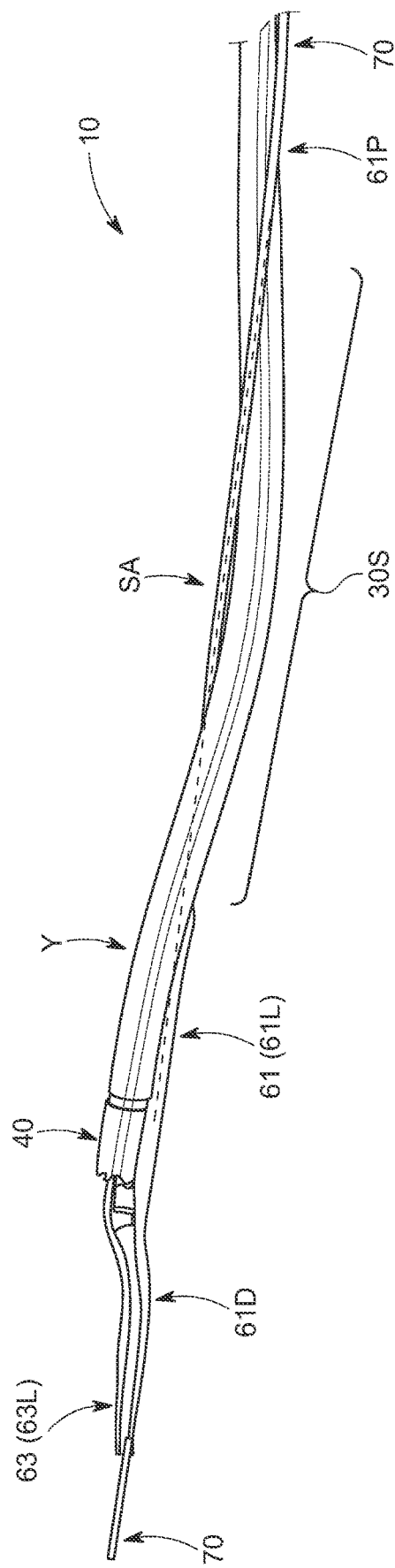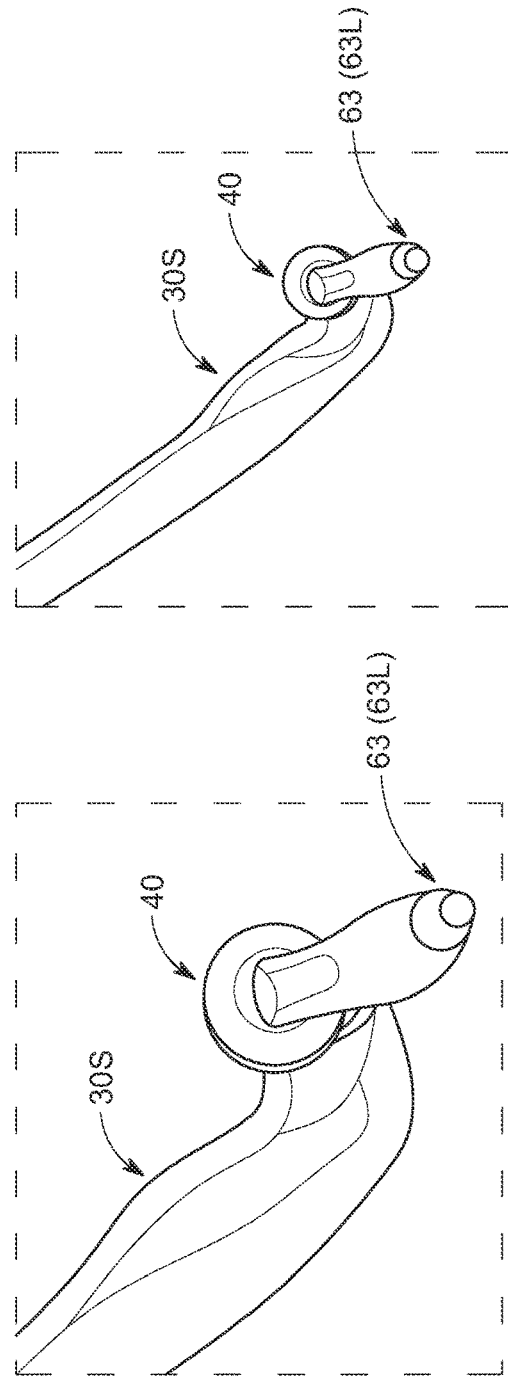
FIG. 5A
FIG. 5B
FIG. 5C

CATHETER HAVING A SPIRAL DRIVE SHAFT

CROSS REFERENCE TO RELATED APPLICATIONS

This patent application claims priority to U.S. Provisional Patent Application No. 63/407,539, titled "CATHETER HAVING A SPIRAL DRIVE SHAFT" and filed on Sep. 16, 2022. This application is herein incorporated by reference in its entirety.

TECHNICAL FIELD

Embodiments of the present disclosure relate generally to a catheter, a medical device, and a method for removing an object in a body lumen.

BACKGROUND

Medical devices that have a catheter including a rotatable drive shaft and a cutting member are widely used to remove an object from a body lumen such as a blood vessel. Such medical devices have a motor for generating torque and a hub for storing mechanism to transmit the generated torque to the cutting member through the drive shaft.

A catheter has at its distal end a guide wire lumen into which a guide wire for guiding the catheter inside a body lumen is inserted. At the beginning of an operation, an introducer sheath is inserted into the body vessel, and then the guide wire is inserted through the sheath toward and beyond a target object to be removed. Subsequently, the guide wire outside the body is inserted into the guide wire lumen of the catheter, which is then inserted into the body lumen along the guide wire. Once the distal end of the catheter has reached the object, the cutting member is rotated, and the catheter is further moved forward so that the cutting member contacts and cuts the object.

A conventional standardized catheter has a cutting diameter of up to 2 mm and thus can effectively cut an object that is present in a body lumen of up to 2 mm. However, using the conventional standardized catheter, it is difficult to effectively cut an object that is present in a body lumen of a larger diameter, e.g., 4 mm.

SUMMARY OF THE INVENTION

In an embodiment, a catheter for removing an object in a body lumen includes a rotatable drive shaft including a spiral portion having a spiral shape near a distal end of the drive shaft, an outer tube surrounding the drive shaft, a cutting member connected to the distal end of the drive shaft to be rotated by the drive shaft with respect to a rotation axis and by which the object is cut, a guide wire tube attached to a distal portion of the outer tube, extending substantially straight along a center spiral axis of the spiral portion, and having a first guide wire lumen, and a distal tip attached to a distal end of the guide wire tube and having a second guide wire lumen extending parallel to the rotation axis and communicating with the first guide wire lumen.

BRIEF DESCRIPTION OF THE DRAWINGS

FIGS. 5A through 5C depict a spiral portion of the catheter.

DESCRIPTION OF EMBODIMENTS

The following detailed description describes a catheter, a medical device, and a method for cutting an object inside a body lumen. In the present specification, a side of the medical device or the catheter which is inserted into a body lumen is defined as a distal side, and the other side of the medical device which is held by an operator during an operation is defined as a proximal side.

Figure 1:
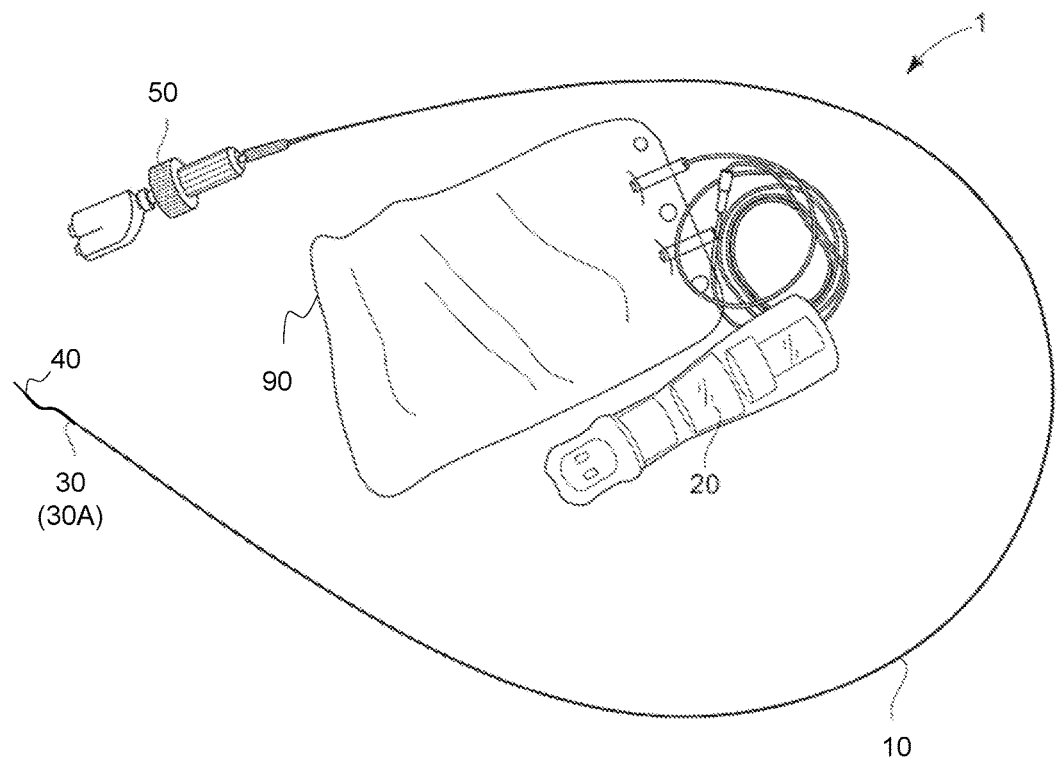
FIGS. 1 and 2 depict a medical device including a catheter and a handle in one embodiment.
Figure 2:
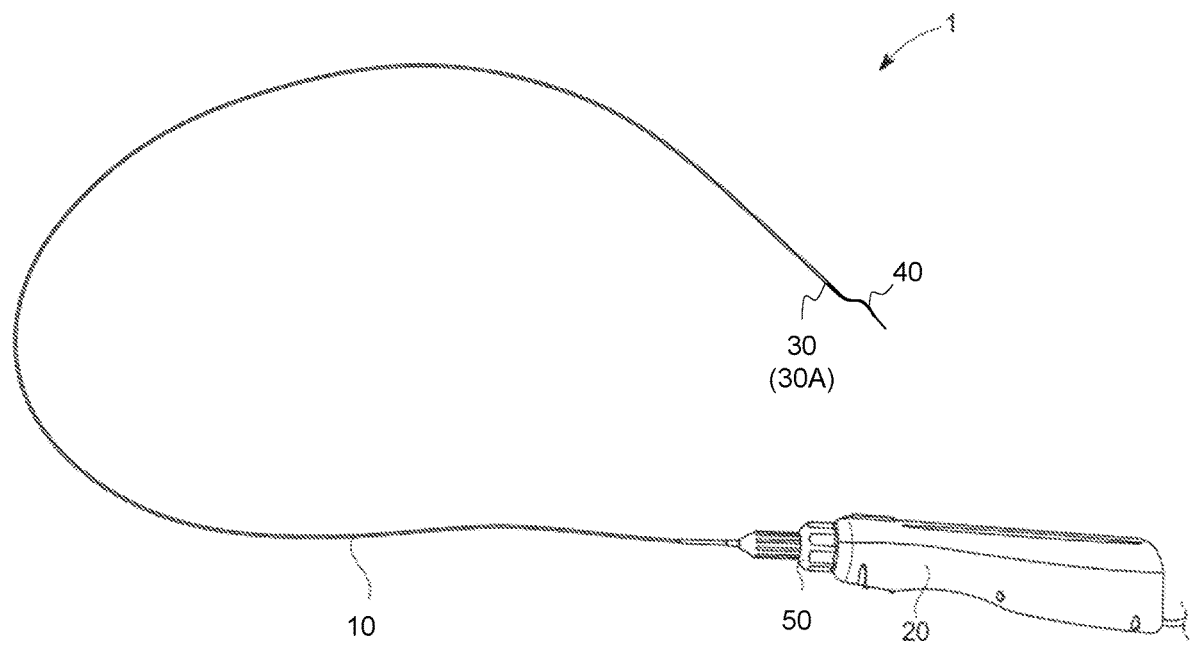

FIGS. 1 and 2 depict a medical device 1 in one embodiment. As shown in the figures, the medical device 1 includes a catheter 10 to be inserted into a body lumen for removing an object and a handle 20 held by an operator. The handle 20 includes a torque generating element such as a motor and an aspiration pump to aspirate the object that has been removed from the body lumen. FIG. 1 shows a state of the medical device 1 in which the catheter 10 is detached from the handle 20, and FIG. 2 shows a state in which the catheter 10 is attached to the handle 20.

The catheter 10 includes an elongated drive shaft 30 surrounded by an outer tube 30A and rotatable therein, and further includes, at its distal end, a cutting member 40 that rotates together with the drive shaft 30 to cut an object. For example, the cutting member 40 is a directional cutter for removing an object located in a particular direction. At the proximal end of the catheter 10, a hub 50 for housing rotating and aspiration mechanisms is attached. The hub 50 can be integrated into the catheter 10 or detachable from the catheter 10.

The drive shaft 30 has the characteristics of being flexible and capable of transmitting rotational power applied from the proximal side to the distal side. Specifically, the drive shaft 30 transmits the rotational torque generated by the torque generating element to the cutting member 40. The drive shaft 30 has an aspiration lumen through which the object that has been cut by the cutting member 40 is moved to the proximal side. The drive shaft 30 penetrates the outer tube 30A, and the cutting member 40 is fixed to the distal end of the drive shaft 30. The proximal portion of the drive shaft 30 is positioned inside of the hub 50.

The drive shaft 30 has a distal opening at which the aspiration lumen opens at the distal end thereof. The distal opening is an entrance into which the cut object enters. The proximal end of the drive shaft 30 is connected to an aspiration port of the hub 50 through which the object that has entered the drive shaft 30 is discharged. The aspirated object is stored in a collection bag 90.

In one embodiment, the drive shaft 30 has, near the distal end thereof, a spiral portion having a spiral shape to increase the effective diameter of the catheter 10 inside a body lumen. A guide wire passes through the center axis of the spiral portion, providing a central support thereof. The detail of the spiral structure is described later with reference to FIGS. 5A-8.

The handle 20 is detachable from the catheter 10 to be reusable in multiple medical procedures. When a medical procedure is performed, the handle 20 is attached to the catheter 10 via the hub 50 so that the drive shaft 30 and the cutting member 40 can rotate according to the torque generated by the torque generating element housed in the handle 20. Thereafter, the drive shaft 30 and the cutting member 40 are inserted into a body lumen, e.g., a vein, using a guide wire. In one embodiment, the hub 50 and the handle 20 may be integrated into a single component so as not to be detachable.

Further details of the aspiration and torque generating mechanisms are described in U.S. application Ser. No. 16/998,824, the entire contents of which are incorporated by reference herein.

Figure 3:
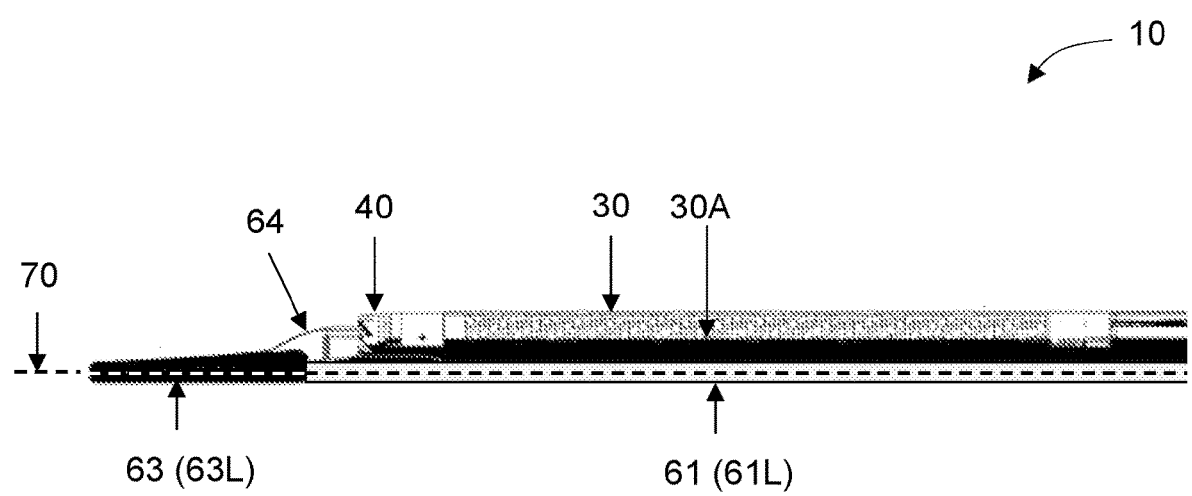
FIGS. 3 and 4 depict a distal portion of the catheter.
Figure 4:
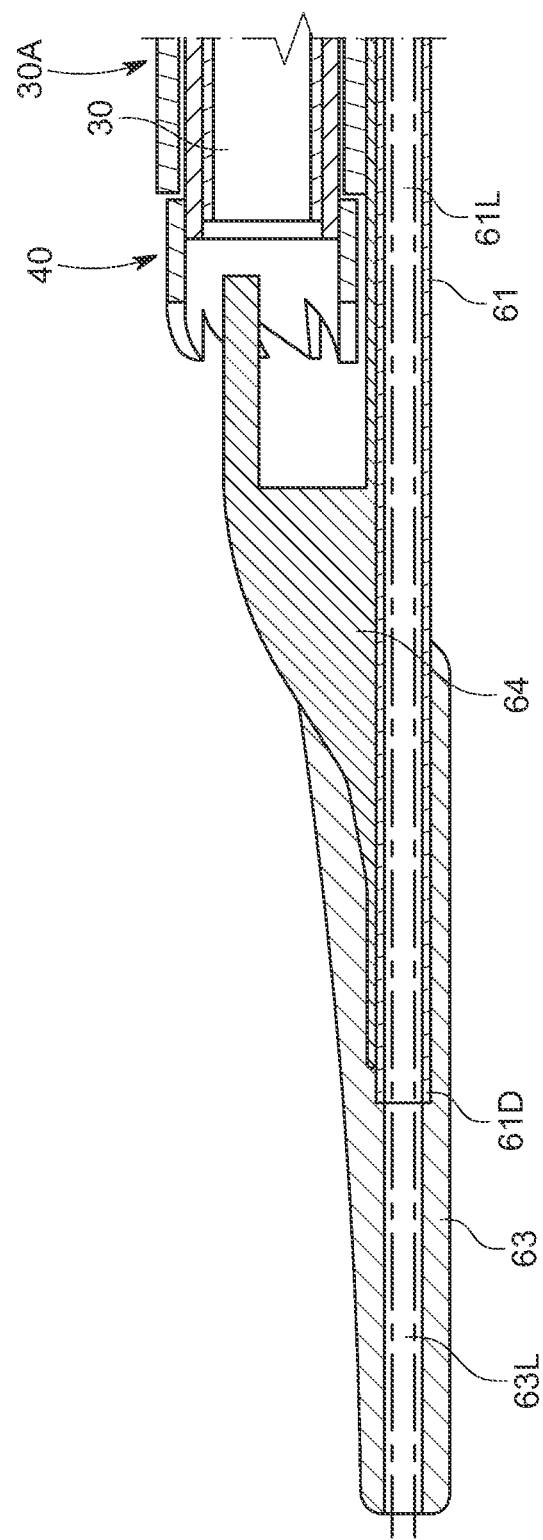

FIGS. 3 and 4 each show a distal portion of the catheter 10. The spiral portion of the catheter 10 is not shown in these figures. As described above, the catheter 10 includes the cutting member 40 at the distal end thereof. The catheter 10 further includes a guide wire tube 61 having a guide wire lumen 61L and a distal tip 63 having a guide wire lumen 63L. The distal tip 63 covers the distal end 61D of the guide wire tube 61 as shown in FIG. 4. During an operation, the catheter 10 is inserted into a body lumen along a guide wire 70 in a state in which the guide wire 70 passes through the guide wire lumens 61L and 63L. That is, the guide wire lumens 61L and 63L form a single path for the guide wire 70 to pass. The catheter 10 and the guide wire 70 are connected to each other inside a body lumen only through the guide wire lumens 61L and 63L.

For example, the guide wire tube 61 is formed of polyimides, PEEK, and the like. The guide wire tube 61 can be fixed to the outer tube 30A by, e.g., a heat-shrinkable tube (not shown) that shrinks at a temperature lower than the guide wire tube 61 so that the guide wire tube 61 is strongly fixed to the outer tube 30A when heated. Alternatively, the guide wire tube 61 can be bonded to the outer tube 30A directly. The distal tip 63 is a resin, preferably a thermoplastic resin, which is softer than the guide wire tube 61 so that the catheter 10 can proceed smoothly inside a body lumen. For example, the distal tip 63 has a length of 1 mm to 50 mm.

FIG. 5A shows a distal portion of the catheter 10 including a spiral portion 30S. In one embodiment, the catheter 10 or the drive shaft 30 has one spiral portion 30S at a position Y near the distal end of the catheter 10 (e.g., 10-30 mm from the distal end of the catheter 10). The spiral portion 30S is longer than the distal tip 63 and has a length of 10-50 mm, for example. FIGS. 5B and 5C depict the distal end of the catheter 10 when viewed from the distal side.

Figure 6:
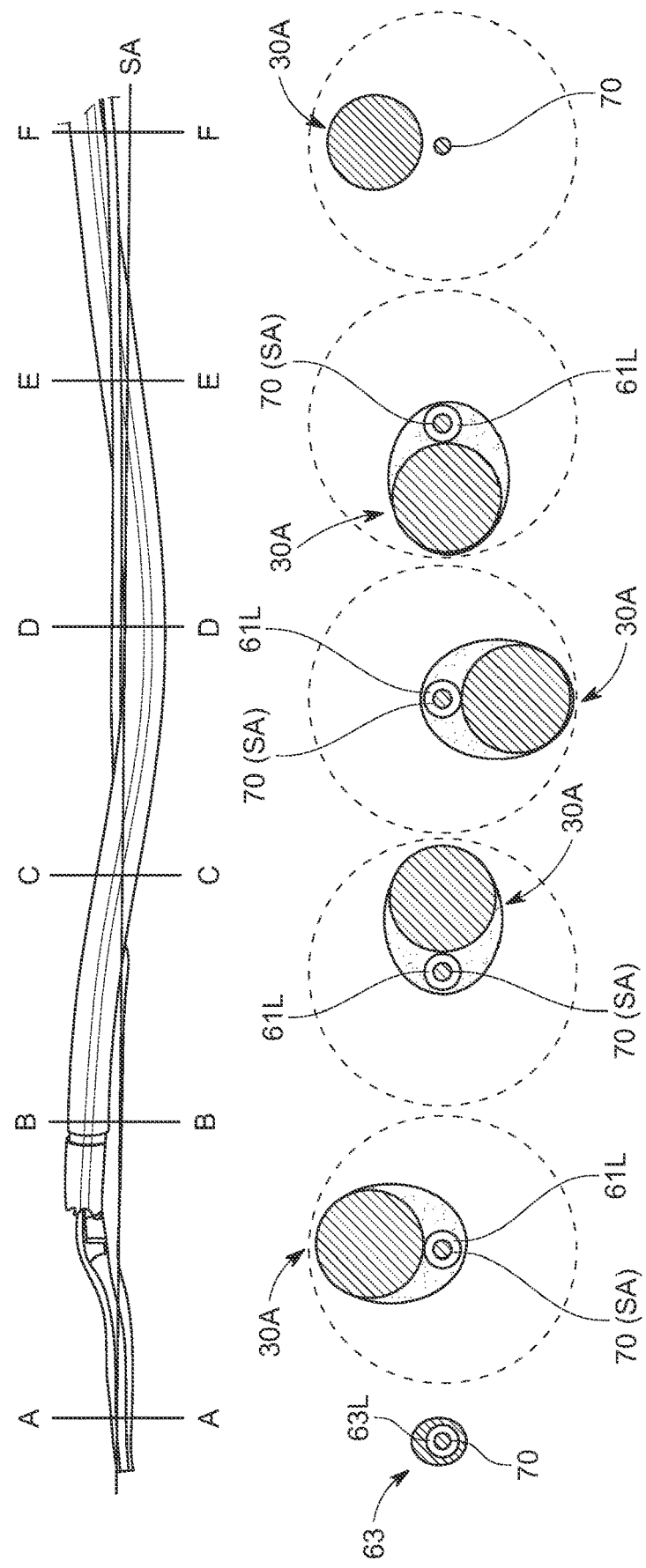
FIG. 6 depicts cross sections of a distal portion of the catheter.

The guide wire tube 61 extends, along the center or spiral axis SA of the spiral portion 30S, from its distal end 61D (see also FIG. 4) to the proximal end 61P that corresponds to the proximal end of the spiral portion 30S. The drive shaft 30 at the spiral portion 30S wraps around the guide wire lumen 61L, which is straight or substantially straight. As a result, the guide wire 70 passes through the center of the spiral portion 30S straight along the guide wire lumen 61L. FIG. 6 shows cross-sections of the distal portion of the catheter 10 taken along lines A-A through F-F. With this configuration, the distal portion of the catheter 10 is well supported by the guide wire 70 and enables better tracking during an operation.

Figure 7:
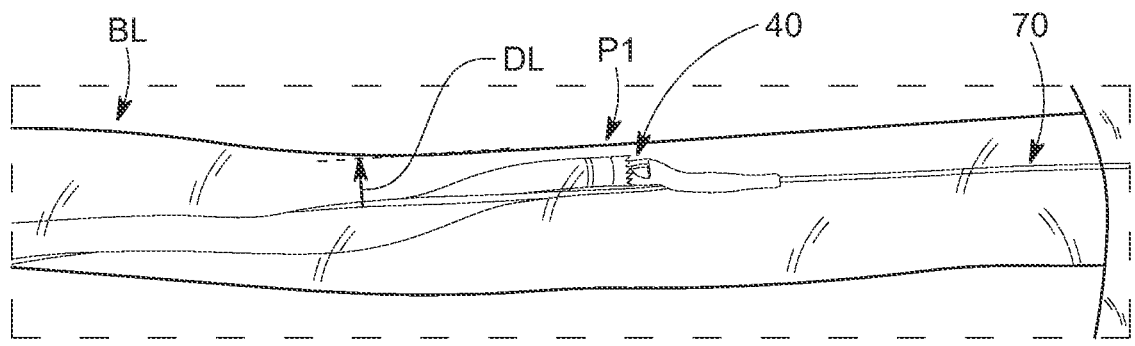
FIGS. 7 and 8 depict a distal portion of a catheter including a spiral portion.
Figure 8:
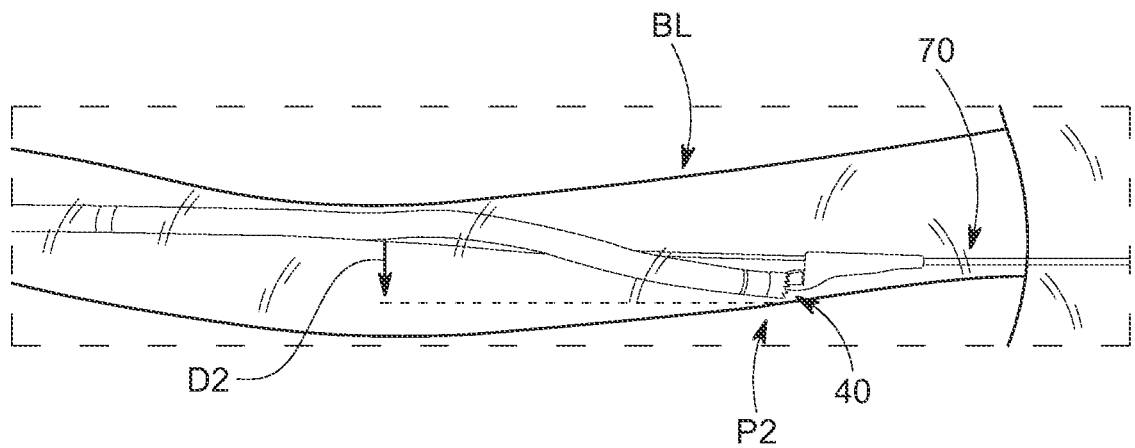

FIGS. 7 and 8 show the catheter 10 guided along a guide wire 70 inside a model of a body lumen BL. Because of its spiral structure, as shown in FIG. 7, the cutting member 40 can be manipulated to a cutting target position P1 on an inner surface of the body lumen BL to remove an object formed thereon. After removing the object at the cutting target position P1, as shown in FIG. 8, the cutting member 40 can be manipulated to a cutting target position P2 on the other side of the body lumen BL. As a result, the effective cutting diameter is increased from D1 corresponding to the cutting diameter that the catheter 10 would be able to achieve without the spiral portion 30S to D2 corresponding to the cutting diameter that the catheter 10 would be able to achieve with the spiral portion 30S.

With reference back to FIGS. 3 and 4, the catheter 10 further includes a stopper 64 on the distal side of the cutting member 40, which stops the cutting member 40 from proceeding further when the catheter 10 is unintentionally pushed into the body lumen. The stopper 64 is formed of a metal material and has a surface that is fixed to the guide wire tube 61 and a portion surrounded by a blade of the cutting member 40. A distal portion of the stopper 64 is covered by the distal tip 63.

Figure 9:
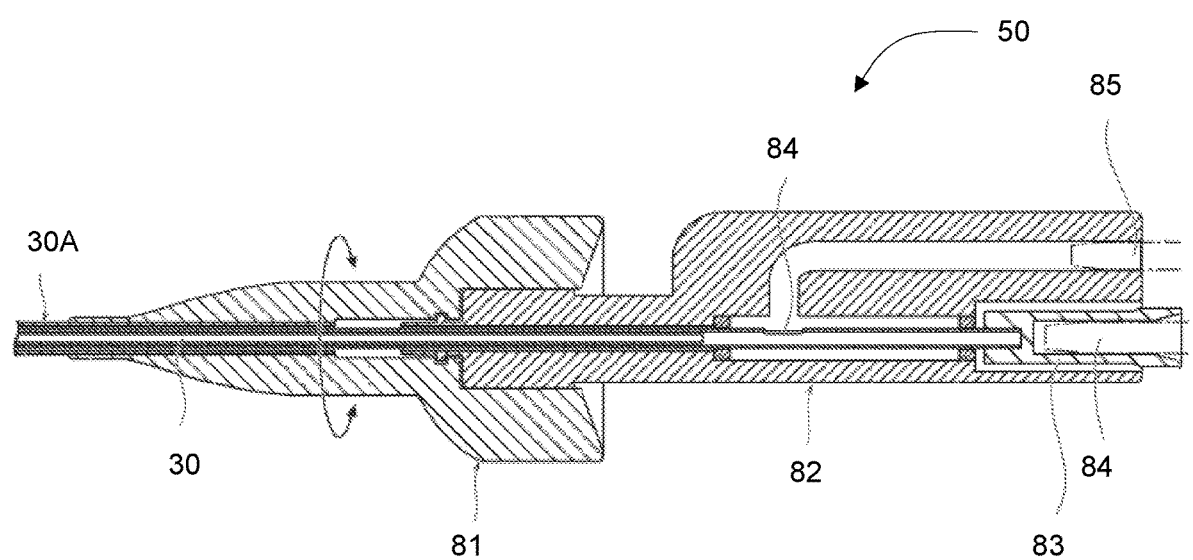
FIG. 9 depicts a proximal portion of a catheter and a hub.

FIG. 9 depicts a proximal portion of the catheter 10 and the hub 50 into which the drive shaft 30 is inserted. The hub 50 includes a rotatable knob 81 and a connector 82 connectable to the handle 20. The knob 81 is connected to the outer tube 30A and manually rotatable by an operator so as to adjust an orientation and/or location of the drive shaft 30 and the cutting member 40 inside a body lumen during an operation. The knob 81 allows the outer tube 30A to rotate independently of the drive shaft 30 and the connector 82.

The drive shaft 30 is, directly or indirectly via one or more other shafts, connected to a coupler 83 with a recess 84 that can engage with a drive shaft (not shown) connected to the torque generating element inside the handle 20. Further, the aspiration lumen of the drive shaft 30 communicates with an aspiration port 85 via an opening 84 inside the connector 82. When the catheter 10 is connected to the handle 20 via the connecter 82, the generated torque is transmitted to the drive shaft 30 via the coupler 83 while the object that has entered the aspiration lumen of the drive shaft 30 is aspirated and discharged from the aspiration port 85 via the opening 84.

Figure 10:
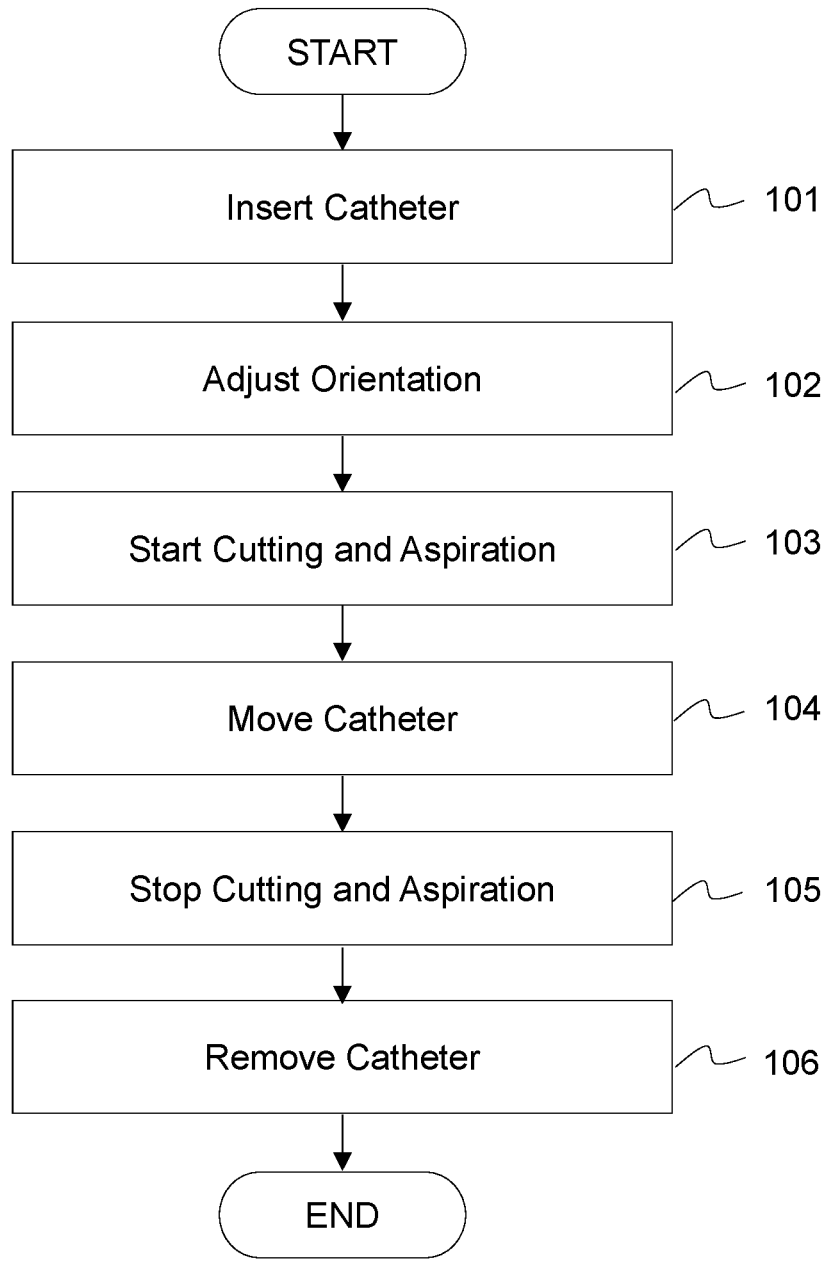
FIG. 10 depicts a flowchart of a method for removing an object in a body lumen.

FIG. 10 depicts a flowchart of a method for removing an object in a body lumen using the medical device 1 or the catheter 10 described above. At the beginning of a medical operation, the operator connects the catheter 10 to the handle 20 via the hub 50 and inserts the guide wire 70 into the body lumen from its distal end using an introducer sheath so that the guide wire 70 reaches and passes near a target location where the object exists. After those steps, the operator passes the proximal end of the guide wire 70 through the guide wire lumens 61L and 63L of the catheter 10, and then inserts the catheter 10 into the body lumen along the guide wire 70 (Step 101).

Once the distal end of the catheter 10 has reached the target location, the operator rotates the knob 81 to adjust the orientation and/or location of the catheter 10 inside the body lumen so that the cutting member 40 is directed toward the object by the spiral structure (Step 102). The operator then turns on the aspiration and torque generating mechanisms of the handle 20 to start cutting and aspirating the object (Step 103), and moves the catheter 10 forward along the guide wire 70 until the target object is removed and aspirated (Step 104).

Once the target object has been removed, the operator turns off the aspiration and torque generating mechanisms (Step 105), and removes the catheter 10 from the body lumen (Step 106). The guide wire and introducer sheath are removed thereafter.

The order of one or more of the steps shown in FIG. 10 can be modified. For example, the aspiration and torque generating mechanisms can be turned on at any time after the catheter 10 has been inserted into the body lumen.

Additionally, one or more of the steps can be repeated if necessary. For example, the orientation of the catheter 10 can be adjusted at any time during the operation to remove the object.

What is claimed is:

1. A catheter for removing an object in a body lumen, comprising:
   a rotatable drive shaft including a spiral portion having a spiral shape near a distal end of the drive shaft;
   an outer tube surrounding the drive shaft;
   a cutting member connected to the distal end of the drive shaft to be rotated by the drive shaft with respect to a rotation axis and by which the object is cut;
   a guide wire tube attached to a distal portion of the outer tube, extending substantially straight along a center spiral axis of the spiral portion, and having a first guide wire lumen; and
   a distal tip attached to a distal end of the guide wire tube and having a second guide wire lumen extending parallel to the rotation axis and communicating with the first guide wire lumen.

2. The catheter according to claim 1, wherein the second guide wire lumen is in line with the center spiral axis of the spiral portion.

3. The catheter according to claim 1, wherein a proximal end of the first guide wire lumen is at a proximal end of the spiral portion.

4. The catheter according to claim 1, wherein a distal end of the first guide wire lumen is between a distal end of the distal tip and the cutting member.

5. The catheter according to claim 1, wherein the spiral portion is located at a distance of 10 mm to 30 mm from a distal end of the distal tip.

6. The catheter according to claim 1, wherein the spiral portion has a length of 10 mm to 50 mm.

7. The catheter according to claim 1, wherein the distal tip has a length of 1 mm to 50 mm.

8. The catheter according to claim 1, further comprising:
   a metal member connected to the guide wire tube, wherein a part of the metal member is surrounded by the cutting member.

9. The catheter according to claim 1, further comprising:
   a knob connected to and rotatable with the outer tube.

10. The catheter according to claim 9, further comprising:
    a hub including the knob and by which the drive shaft is connectable to a motor for generating rotation torque.

11. A medical device for removing an object in a body lumen, comprising:
    a handle including a motor configured to generate rotation torque; and
    a catheter connectable to the handle and including:
       a drive shaft rotatable by the generated rotation torque and including a spiral portion having a spiral shape near a distal end of the drive shaft,
       an outer tube surrounding the drive shaft,
       a cutting member connected to a distal end of the drive shaft to be rotated by the drive shaft with respect to a rotation axis and by which the object is cut,
       a guide wire tube attached to a distal portion of the outer tube, extending substantially straight along a center spiral axis of the spiral portion, and having a first guide wire lumen, and
       a distal tip attached to a distal end of the guide wire tube and having a second guide wire lumen extending parallel to the rotation axis and communicating with the first guide wire lumen.

12. The medical device according to claim 11, wherein the second guide wire lumen is in line with the center axis of the spiral portion.

13. The medical device according to claim 11, wherein a proximal end of the first guide wire lumen is at a proximal end of the spiral portion.

14. The medical device according to claim 11, wherein a distal end of the first guide wire lumen is between a distal end of the distal tip and the cutting member.

15. The medical device according to claim 11, wherein the spiral portion is located at a distance of 10 mm to 30 mm from a distal end of the distal tip.

16. The medical device according to claim 11, wherein the spiral portion has a length of 10 mm to 50 mm.

17. The medical device according to claim 11, wherein the distal tip has a length of 1 mm to 50 mm.

18. The medical device according to claim 11, wherein the catheter further includes a metal member connected to the guide wire tube, a part of the metal member being surrounded by the cutting member.

19. The medical device according to claim 11, further comprising:
    a hub by which the catheter is connectable to the handle so that the generated rotation torque is transmitted from the motor to the drive shaft, and
    a knob connected to and rotatable with the outer tube.

20. A method for removing an object in a body lumen using a catheter that includes:
    a rotatable drive shaft including a spiral portion having a spiral shape near a distal end of the drive shaft,
    an outer tube surrounding the drive shaft,
    a cutting member connected to the distal end of the drive shaft to be rotated by the drive shaft with respect to a rotation axis and by which the object is cut,
    a guide wire tube attached to a distal portion of the outer tube, extending substantially straight along a center spiral axis of the spiral portion, and having a first guide wire lumen, and
    a distal tip attached to a distal end of the guide wire tube and having a second guide wire lumen extending parallel to the rotation axis and communicating with the first guide wire lumen, the method comprising:
    inserting the catheter into the body lumen;
    positioning the cutting member to a first target cutting position on a first side of the body lumen and removing an object formed thereon;
    positioning the cutting member to a second target cutting position on a second side of the body lumen that is opposite to the first side and removing an object formed thereon; and
    removing the catheter from the body lumen.

\* \* \* \* \*